United States Patent [19]
Ward

[11] Patent Number: 5,906,298
[45] Date of Patent: May 25, 1999

[54] SCENT DISPERSAL SYSTEM

[76] Inventor: Thomas A. Ward, 1942 Kristy La., Holts Summit, Mo. 65043

[21] Appl. No.: 08/885,633

[22] Filed: Jun. 30, 1997

[51] Int. Cl.⁶ .................................................. B67D 5/64
[52] U.S. Cl. ................................ 222/175; 43/1; 222/187; 239/36; 239/50
[58] Field of Search .............................. 222/1, 175, 187; 259/36, 47, 49, 50; 43/1

[56] References Cited

U.S. PATENT DOCUMENTS

| | | | |
|---|---|---|---|
| 2,786,714 | 3/1957 | Saleny | 239/50 |
| 5,074,439 | 12/1991 | Wilcox | 222/175 |
| 5,148,949 | 9/1992 | Luca | 222/175 |
| 5,566,869 | 10/1996 | Katz | 222/175 |
| 5,622,314 | 4/1997 | Eason | 239/47 |

FOREIGN PATENT DOCUMENTS 935150  10/1955  Germany ................................ 222/187

*Primary Examiner*—Joseph A. Kaufman
*Attorney, Agent, or Firm*—Richard J. Grundstrom

[57] ABSTRACT

The scent dispersal system of this invention includes a reservoir for holding a liquid scent, a cap to close an opening in the reservoir, a conduit extends outward from the cap, a wick extends from the reservoir's interior to the exterior via the conduit and a way is provided to attach the scent dispersal system to an individual. A wick retainer is used to prevent pulling the wick from the reservoir and to retain the end of the wick in the liquid scent. A tube plug is used to close and seal the end of the conduit. Through capillary action the scent is automatically drawn to an exposed end of the wick extending outward from the end of the conduit. The scent is automatically dissipated or dispersed from the exposed end of the wick. As one walks, the scent creates a trail by rubbing off on grasses, leaves or other flora in the woods. At a fixed location the scent is dissipated by evaporation from the wick. Strength of the scent is controlled by the amount of the wick exposed.

12 Claims, 4 Drawing Sheets

SCENT DISPERSAL SYSTEM

BACKGROUND OF THE INVENTION

The present invention relates to a scent dispersal system and more particularly to an automatic system for the dispersal of liquid scent.

Liquid scents are often used by hunters and others to mask the human oder or to attract a particular species of animal. This is to increase the odds of attracting and observing the animals of the wild. Hunters are probably the most common users of such scents but other nature lovers also use scents as such. In addition to hunting, scents are used during nature photography, wildlife studies, by hikers who want to observe wildlife and by others who in general want to observe wild life.

There are many scents available on the market for attracting various species of wild life. All claim and do have various differences, advantages and disadvantage from one another. Whether one is better than another is often in the judgment of the user.

Just as there are many different types of scents, there are different methods of application or use. This invention addresses a method of dispersing a scent.

The most common method of use is to place cotton or other absorbent material into an open container. The scent is poured onto the absorbent material and the open container is placed in a desired position. Often multiple containers are used to surround an area to more resemble a natural dispersal of an animal scent. One disadvantage is that this is a fixed area dispersal. If there is a desire to move the containers must be also be moved. Additionally, the time required to prepare and place the open containers of scent adds up. This is a manual method of application.

Another method is to apply the scent directly to the clothing of the individual. This could be pant legs, arms or even boots. The disadvantage of this method is that it is messy and clothing becomes scented or stained and only a fixed or limited amount of scent can be applied. As the scent dissipates and dries, or becomes diluted or washed off by wet grasses, rain or walking through water, additional scent has to be applied and reapplied. Again this can be messy and time consuming.

An absorbent pad attached to the individual is another method. This method prevents clothing from being scented. Still the disadvantage remains that only a little scent can be applied and must be reapplied in a short time.

Yet another method uses an absorbent pad attached to an individual by a cord. The scent is applied to the absorbent pad. The absorbent pad is pulled behind the individual as they walk. By applying scent in this manner, the scent rubs off on the trail, ground or surrounding grasses. This leaves a scent trail. But as the trail is being made, the scent is diluted as the individual walks. This results in a strong scent at the beginning and a weak scent trailing off to no scent at the end.

The advantage of the last methods is that trails can be made by the scents as one walks through the woods or along trails. It is desirable to leave a trail of certain scents that animals will find and follow. This often leads the animal right to the individual making the trail. But again the disadvantage is the limited amount of scent that can be used in making a trail.

One major disadvantage of these prior methods is that once a scent is applied, the scent remains until diluted, washed off, evaporated or otherwise eliminated. Once a scent is used there is no recovery when done. This results in excessive amounts of scent being wasted. In addition you cannot "shut off" the scent when done. Additionally, there is no easy way to control the strength of the scent or scent trail. Once applied, that is the initial strength of the scent and through the dissipation and evaporation the strength diminishes rapidly.

Accordingly, it is an object of the present invention to provide a scent dispersal system that overcomes the disadvantages of other method of use and to maintain and enhance the advantages. With the scent dispersal system of this invention a large quantity of liquid scent can be used, the method of dispersal is automatic and not messy. Clothing and parts of the body are not stained or scented. Plus a trail of scent can be left without the dilution of the trail or scent as the individual walks.

Another object of the present invention is to provide an improved scent dispersal system that is easy to construct and simple to use.

A further object of the present invention is to provide a scent dispersal system adapted for use with a wide variety of different scents to thereby substantially eliminate all other methods of application and use. With this invention any liquid scent can be used. Trails are easily and automatically made as one walks along trails or through grass or woods. Plus the invention provides an easy method to establish a fixed location of scent if desired.

Still another object of the present invention is to provide a scent dispersal system that may be open and closed at any time. When open the scent will be dispersed and when closed the liquid scent contained therein will be conserved and "shut off" until the next use.

SUMMARY OF THE INVENTION

To accomplish the foregoing and other objects of this invention there is provided a scent dispersal system and more particularly a liquid reservoir that attaches to the leg and has a wick extending from the cap. As a person walks the scent is disperse via the wick. The wick absorbs the liquid scent and through capillary action rises the scent to the exposed end of the wick.

The scent dispersal system of this invention includes a liquid reservoir with a central opening at the top. A cap is used to close the opening of the reservoir. A flexible conduit extends from an opening through the cap. The wick extends through the conduit into the liquid scent in the reservoir.

Through capillary action the scent is automatically drawn to an exposed end of the wick extending outward from the end of the conduit. The scent is automatically dissipated or dispersed from the exposed end of the wick. As one walks, the scent creates a trail by rubbing off on grasses, leaves or other flora in the woods. At a fixed location the scent is dissipated by evaporation from the wick.

The wick retainer is used to prevent the wick from being pulled from the conduit and to ensure the wick remains in the liquid scent. A tube plug is also included to seal or close the end of the conduit when not in use. This feature allows the wick to be slid back into the conduit and reservoir when done. This seals off the scent for future use and prevents additional evaporation or dispersal of the liquid scent.

The above mentioned objectives and other objects and features of the present invention will be better understood and appreciated from the following detailed description of the main embodiment thereof, selected for purposes of illustration and shown in the accompanying drawings.

DETAILED DESCRIPTION

Figure 1:
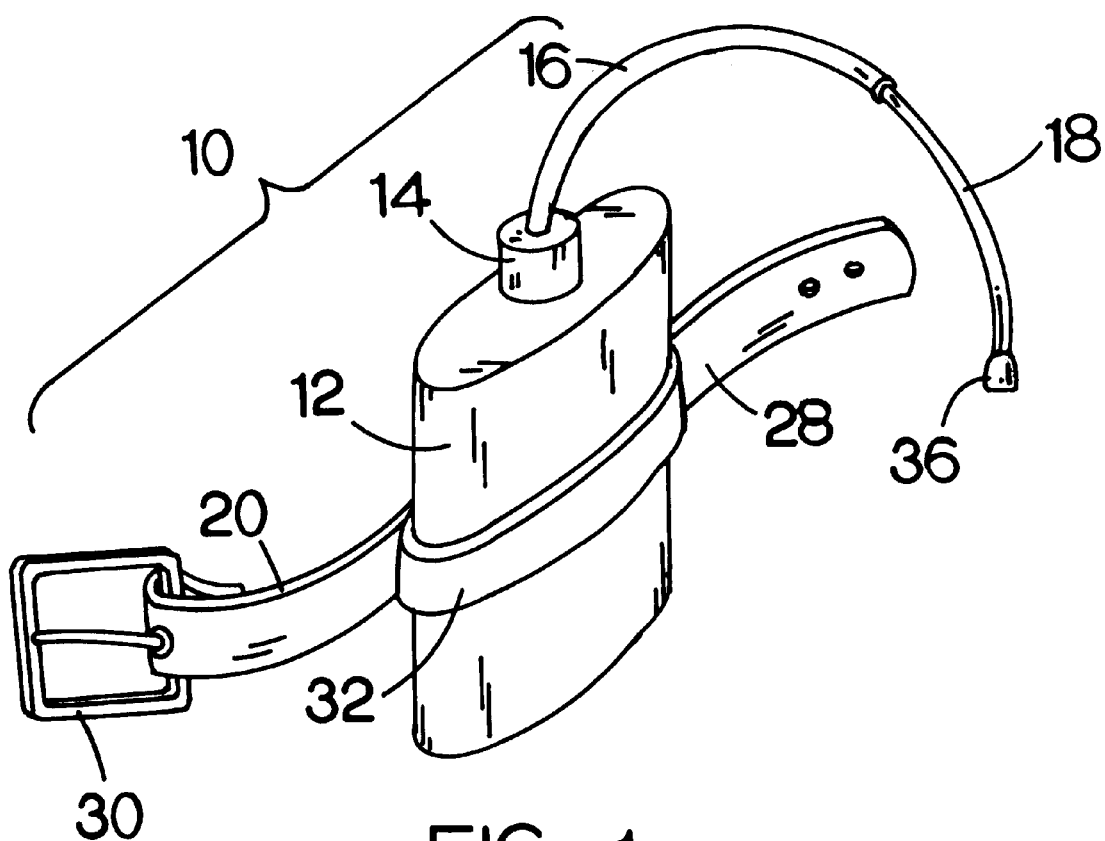
FIG. 1 is an isometric view of the scent dispersal system.

Referring now to the drawings there is shown the preferred embodiments of the scent dispersal system. Generally, the simple embodiment of the scent dispersal system 10 consists of a reservoir 12 for holding a liquid scent 26, cap 14 to close an opening in the reservoir 12, conduit 16 extending from the cap 14, a wick 18 extending from the reservoir interior to the exterior via the conduit 16 and an attachment means 20 to attach the scent dispersal system to an individual. A wick retainer 22 to prevent pulling the wick from the reservoir 12 and a tube plug 36 to plug and seal the end of the conduit are also provided as additions to the basic embodiment. The scent dispersal system of this invention can be used attached to an individual or as a stand alone fixed dispenser.

The preferred embodiment and the best mode contemplated of the scent dispersal system 10 of the present invention are herein described. However, it should be understood that the best mode for carrying out the invention hereinafter described is offered by way of illustration and not by the way of limitation. It is intended that the scope of the invention includes all modifications which incorporate its principal design features.

Figure 2:
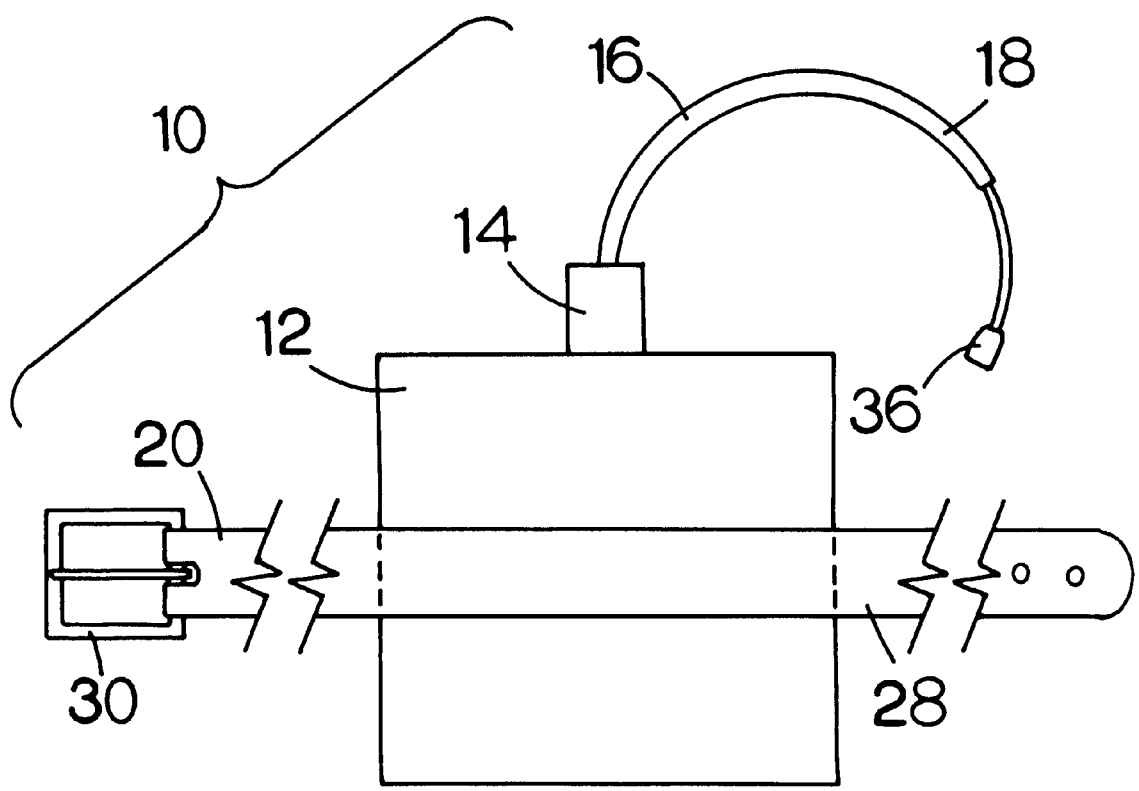
FIG. 2 is a front view of the scent dispersal system showing a strap and buckle attachment means.
Figure 3:
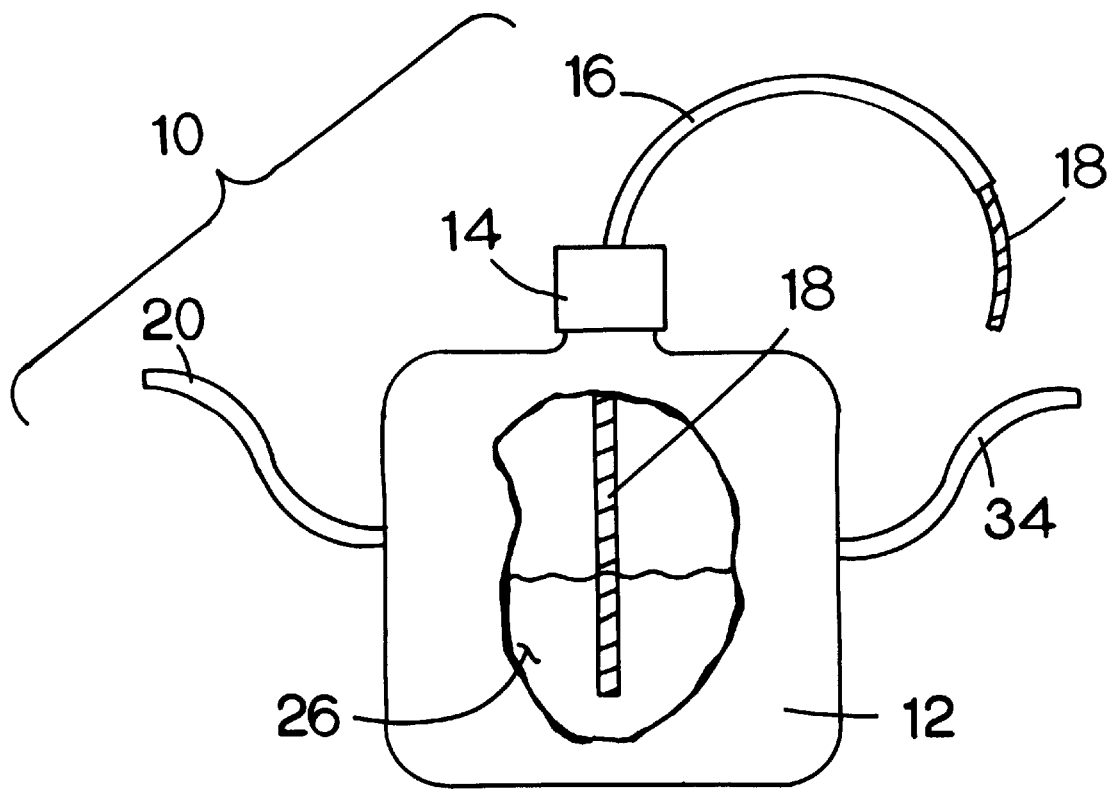
FIG. 3 is another front view of the scent dispersal system having a partial cutaway view of the reservoir to show the liquid scent and wick therein.

The reservoir 12 is a liquid holding apparatus such as a bottle, flask or other container. It can be made of plastic, metal or any other suitable material. The reservoir 12 general requirements are that it contains liquid and is small and light enough to be conveniently attached to an individual. Once attached the reservoir must not create an unreasonable amount of inconvenience in movement. The reservoir 12 must have an opening for filling the reservoir with the liquid scent 26. In general the reservoir also must have a back side, front side, and a bottom. In the preferred embodiment the reservoir 12 is a plastic flask, as shown in FIGS. 1, 2 and 3. However, any suitable container would also function as the reservoir without departing from the scope and intent of this invention.

The reservoir 12 can be sitting at a fixed location or the reservoir can be attached to the lower portion of an individual's leg. It can be used in either manner at the desires of the individual. In the later position, the wick 18 dispenses the scent as the individual walks. A trail can be created by the wick rubbing against grasses, brush or other flora along the way. In order for the reservoir to be attached there is provided an attachment means 20. The attachment means is generally affixed to the reservoir 12 in accordance with the specific type of attachment means 18 employed.

The attachment means 18, as shown in FIGS. 1 and 2 consist of a strap 28 and a buckle 30. The strap can be attached to the reservoir 12 in any acceptable manner. As shown in FIG. 1, the strap 28 contains a loop 32 for securing the reservoir 12. The strap 28 is wrapped around a lower portion of an individual's leg and secured by buckle 30.

In another embodiment shown in FIG. 3, the attachment means 18 consists of a simple cord 34. The cord 34 is affixed to the reservoir 12. The cord 34 is wrapped around and tied to an individual for attaching the scent dispersal system 10 to the individual.

An alternative to the buckle 30, which is not shown since the concept can be understood without a drawing, is to replace the buckle with typical hook and loop fasteners well known in the art. The hook and loop material would be attached to each end of the strap 28. The strap 28 would be attached to the reservoir 12 as suggested above. The strap 28 is wrapped around a lower portion of an individual's leg and secured on the leg by the hook and loop material.

An alternative to attach the reservoir 12 to the attachment means, not shown, is to provide a carrying case. The carrying case would be similar to a canteen carrying case. The carrying case would contain a pocket for the reservoir and would be secured to an individual by a strap 28.

A cap 14 is furnished to provide a means of closing and sealing the opening in the reservoir 12. The cap 14, in the preferred embodiment, has a central opening for receiving the conduit 16. Typically, the cap 14 has a threaded female opening that screws onto a threaded male receptacle on the reservoir 12.

The conduit 16, in the preferred embodiment, is a somewhat flexible plastic tube. The conduit 16 provides the path for the wick 18 and positions the exposed portion of the wick 18 at a predetermined distance from the individual. The conduit 16, in the preferred embodiment, is attached to the central opening located through the top of the cap 14. However, the conduit 16 can be extended from anywhere on the reservoir, top, sides or any other location, without departing from the scope and inventive concepts herein disclosed. The conduit 16 is open on the inside of the reservoir 12 and extends outward from the reservoir 12. In the preferred embodiment, the length of the conduit is typically four inches. However, the length can be made shorter or longer, depending on the desires of the individual.

The wick 18 is a standard wick known in the art. The wick 18 is sized to correctly fit and slide within the conduit 16. The wick slides from an in-storage-position to an extended in-use-position. The inside end of the wick 18 sits within the liquid scent 26 contained within the reservoir 12. The outer end extends from the outward end of conduit 16. The length of the wick 18 is determined by the length of the conduit, the distance from the inside of the cap to the bottom of the reservoir and the exposed length desired by the individual.

In the in-use-position a predetermined length of the wick 18 would extend from the end of conduit 16. The wick 18 would be slid back into the conduit 16 and into the reservoir 12 for storage in the in-storage-position, when not in use. By adjusting the length of the exposed portion of the wick 18 the strength of the scent can be controlled. The more wick 18 exposed the stronger the scent. On the other hand, the shorter the exposed wick 18 the weaker the scent. The strength of the scent remains constant as long as there is liquid scent 26 contained within the reservoir. No prior art has such advantages.

To conserve the liquid scent 26 a tube plug 36 is provided. The tube plug 36 attaches to the end of the wick 18 such that as the wick 18 is slid back into the conduit 16, the tube plug 36 seals the end of the conduit 16. This prevents any additional evaporation of the liquid scent 26 and essentially "turns off" the scent dispersal. With the end of the conduit sealed, spills and accidental scenting is eliminated. Again, no prior art has such advantages.

To use the scent dispersal system 10, the reservoir is attached to the leg of the individual and the wick 18 is pulled from the conduit 16. The tube plug 36 functions as a handle in this regard. In the preferred embodiment, the tube plug 36 is made from a soft plastic material. The tube plug 36 is generally tapered such that the narrow end easily inserts into the end of the conduit 16.

To prevent the wick from being pulled completely out of the conduit 16 and to ensure the inside end of the wick 18 remains within the liquid scent 26, a wick retainer 22 is provided. The wick retainer 22 attaches to a portion of the wick 18 inside of the reservoir 12 in a position such that the wick retainer 22 hits the inside surface of the cap 14 as the wick 18 is pulled outward into the in-use-position. The lower or inside end of wick 18 when wick retainer 22 is engaged with the inside of the cap 14, is positioned at the bottom of the reservoir. This ensures that the wick 18 remains in the liquid scent 26 when pulled out to the maximum in-use-position.

Figure 4:
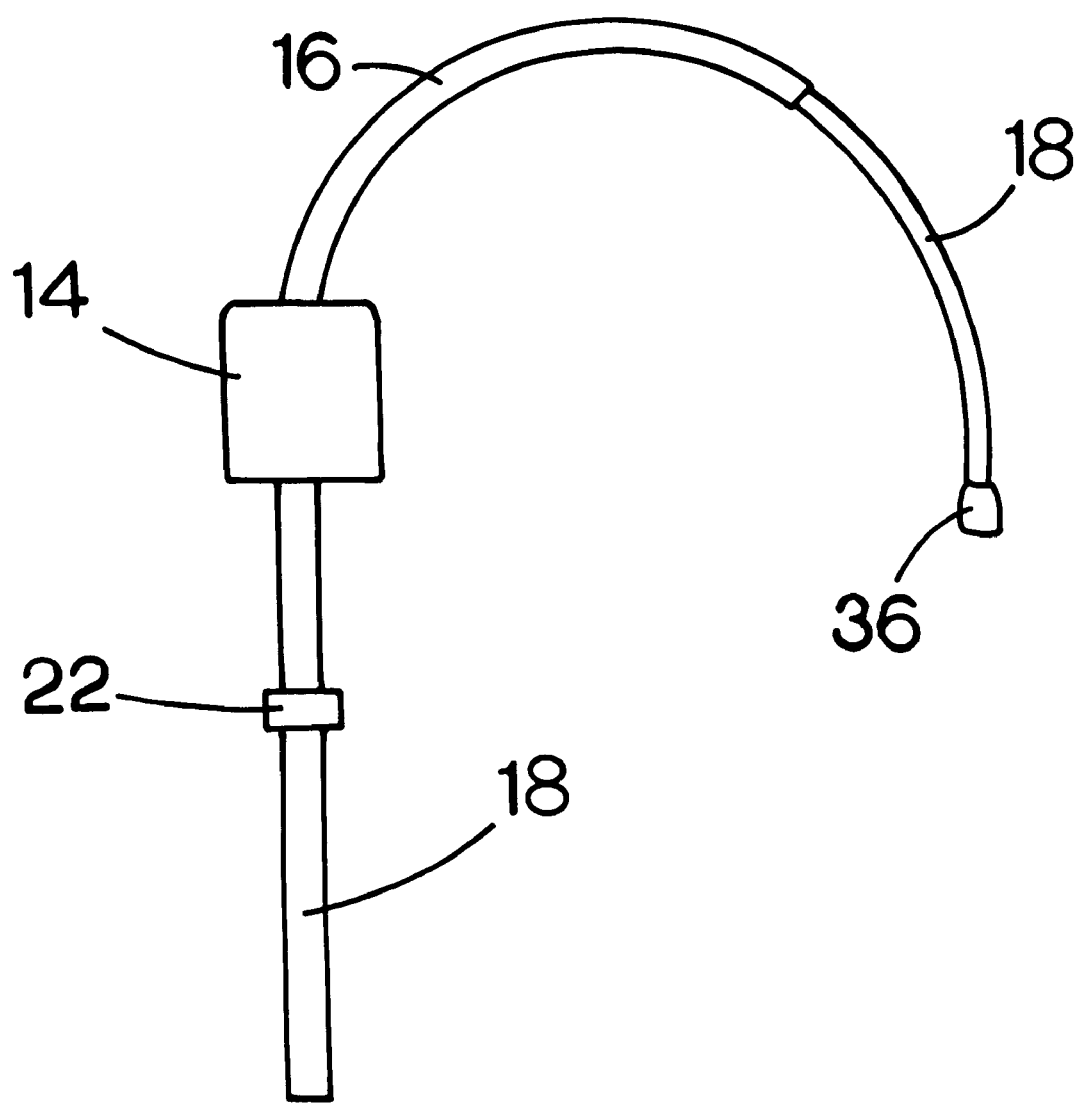
FIG. 4 is a view showing the relationship of the cap, wick, wick retainer, conduit, and tube plug.

In the preferred embodiment, the wick retainer 22, as shown on FIG. 4, is a ring clip that surrounds and attaches securely to the wick 18. The wick retainer 22 must be securely tightened to the wick 18 to prevent the wick 18 from being pulled from the reservoir 12 and conduit 16 but it cannot be tightened to a point of stopping the capillary action of the wick 18.

In a simple embodiment, not shown, the wick retainer 22 is a simple knot properly positioned on the wick 18.

Having described the invention in detail, those skilled in the art will appreciate that modifications may be made of the invention without departing from the spirit of the inventive concept herein described.

Therefore, it is not intended that the scope of the invention be limited to the specific and preferred embodiments illustrated and described. Rather, it is intended that the scope of the invention be determined by the appended claims and their equivalents.

What is claimed is:

1. A scent dispersal system comprising:
   a reservoir for holding a liquid scent, said reservoir having an opening for filling said reservoir, a back side, front side, and bottom;
   an attachment means for attaching said reservoir to an individual, said attachment means affixed to said reservoir;
   a cap having a central opening to cover and close said top opening on said top of said reservoir;
   a conduit extending outward from said central opening in said cap; and
   a wick, said wick being slidable within said conduit from an in storage position to an extended in use position, said wick extending from liquid scent contained within said reservoir, through said conduit and outward from an outward end of said conduit for a predetermined length in said in use position and being slidable into said reservoir for an in storage position.

2. The scent dispersal system as set forth in claim 1 further comprising a tube plug contained on an outer end of said wick, said tube plug sealing said outer end of said conduit when said wick is slid into said reservoir in said in storage position.

3. The scent dispersal system as set forth in claim 1 further comprising wick retainer, said wick retainer attached to a portion of said wick in a position that said wick retainer engages an inside surface of said cap when said wick is slid outward into said in use position, said wick retainer preventing said wick from being pulled out of said conduit and maintains a lower end of said wick in said liquid scent within said reservoir.

4. The scent dispersal system as set forth in claim 1 in which said attachment means comprises a strap and buckle, said strap being attached to said reservoir, said strap being secured to a lower portion of an individual's leg by said buckle.

5. The scent dispersal system as set forth in claim 1 in which attachment means comprises a strap having hook and loop fasteners on ends of said strap, said strap being attached to said reservoir and wrapped around a lower portion of an individual's leg and secured on the leg by said hook and loop material.

6. The scent dispersal system as set forth in claim 1 in which attachment means comprises a carrying case and a strap attached to said carrying case, said reservoir securely fitting within said carrying case, said strap securing said carrying case to an individual.

7. The scent dispersal system as set forth in claim 1 in which said wick retainer comprises a properly positioned knot on said wick.

8. The scent dispersal system as set forth in claim 1 in which wick retainer comprises a clip properly positioned and attached and secured to said wick.

9. The scent dispersal system as set forth in claim 2 in which said tube plug comprises a soft flexible plastic material having a tapered shape attached to said outer end of said wick, a narrow end of said tube plug fitting within an outer end of said conduit to seal said end of said conduit.

10. The scent dispersal system as set forth in claim 1 in which said attachment means comprises a cord affixed to said reservoir, said cord tied to an individual for attaching said reservoir to the individual.

11. A scent dispersal system comprising:
    a reservoir for containing liquid scent;
    a conduit extending from said reservoir;
    a wick extending outward from said liquid scent contained within said reservoir through said conduit, said wick being slidable within said conduit;
    a retaining means to prevent said wick from being pulled completely out of said conduit and for retaining an end of said wick within said liquid scent in said reservoir; and
    a means to seal and close said conduit when said scent dispersal system is not in use.

12. The scent dispersal system as set forth in claim 11 further claiming an attachment means, said attachment means being affixed to said reservoir for attaching said scent dispersal system to an individual.

* * * * *